United States Patent
Sauser et al.

(10) Patent No.: US 9,700,239 B2
(45) Date of Patent: Jul. 11, 2017

(54) FLUIDIZABLE BED WITH OCCUPANCY STATUS DETECTION AND METHOD OF OCCUPANCY STATUS DETECTION FOR A FLUIDIZABLE BED

(71) Applicants: Frank Sauser, Cincinnati, OH (US); Kristopher Klink, Indianapolis, IN (US)

(72) Inventors: Frank Sauser, Cincinnati, OH (US); Kristopher Klink, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 260 days.

(21) Appl. No.: 13/651,639

(22) Filed: Oct. 15, 2012

(65) Prior Publication Data

US 2014/0009293 A1    Jan. 9, 2014

Related U.S. Application Data

(60) Provisional application No. 61/668,534, filed on Jul. 6, 2012, provisional application No. 61/670,309, filed on Jul. 11, 2012.

(51) Int. Cl.
*A61B 5/11* (2006.01)
*A61B 5/00* (2006.01)
(Continued)

(52) U.S. Cl.
CPC .......... *A61B 5/1115* (2013.01); *A61B 5/6891* (2013.01); *A61G 7/05746* (2013.01);
(Continued)

(58) Field of Classification Search
CPC ...... A61B 2562/0247; A61B 2562/168; A61B 5/1115; A61B 5/6891; A61G 2203/34;
(Continued)

(56) References Cited

U.S. PATENT DOCUMENTS 4,483,029 A    11/1984  Paul
5,623,736 A *  4/1997  Soltani ............... A61G 7/05746
                                              5/689

(Continued)

FOREIGN PATENT DOCUMENTS

FR    2550442 A1    2/1985
WO    0057830 A1    10/2000

OTHER PUBLICATIONS

European Search Report for EP Application 13172790; Place of Search—The Hague; Date of completion of the search—Oct. 30, 2013.

*Primary Examiner* — Laura Nguyen
(74) *Attorney, Agent, or Firm* — Barnes & Thornburg, LLP

(57) ABSTRACT

A method of detecting a change in occupancy status of a fluidizable bed (10) includes determining (102) an unloaded plenum pressure value corresponding to the absence of a load on the bed, determining (104) a loaded plenum pressure value corresponding to the presence of an occupant on the bed, and establishing a reference ($P_{REF}$) as a function of at least one of the unloaded plenum pressure value and the loaded plenum pressure value. A signal (116, 120) is issued in response to a relationship between the reference and a value ($P_{MON}$) representative of actual pressure in the plenum. The bed also includes a pressure sensor (60) for monitoring a pressure value representative of pressure in the plenum and a controller (50) for issuing a signal (116, 120) responsive to a relationship between the monitored value and a reference value.

11 Claims, 5 Drawing Sheets

(51) Int. Cl.
*A61G 7/057* (2006.01)
*A61G 7/07* (2006.01)

(52) U.S. Cl.
CPC ........ *A61G 7/07* (2013.01); *A61B 2562/0247* (2013.01); *A61B 2562/168* (2013.01); *A61G 2203/34* (2013.01)

(58) Field of Classification Search
CPC ...... A61G 7/05746; A61G 7/07; A61G 7/018; Y10S 5/94
See application file for complete search history.

(56) References Cited

U.S. PATENT DOCUMENTS

| | | | |
|---|---|---|---|
| 6,721,979 B1 | 4/2004 | Vrzalik et al. | |
| 2003/0191382 A1* | 10/2003 | Luce | A61B 3/165 600/401 |
| 2004/0158927 A1* | 8/2004 | Soltani | A61G 7/05746 5/689 |
| 2009/0192364 A1* | 7/2009 | Voto et al. | 600/301 |
| 2009/0307505 A1* | 12/2009 | Robertson | G06F 1/266 713/300 |
| 2010/0088825 A1 | 4/2010 | Howell et al. | |
| 2010/0229310 A1* | 9/2010 | Howell | A61G 7/05746 5/689 |
| 2011/0041254 A1* | 2/2011 | Howell | A61G 7/05746 5/689 |
| 2011/0302720 A1 | 12/2011 | Yakam et al. | |
| 2016/0158083 A1* | 6/2016 | Lambarth | A61G 1/0268 5/600 |

* cited by examiner

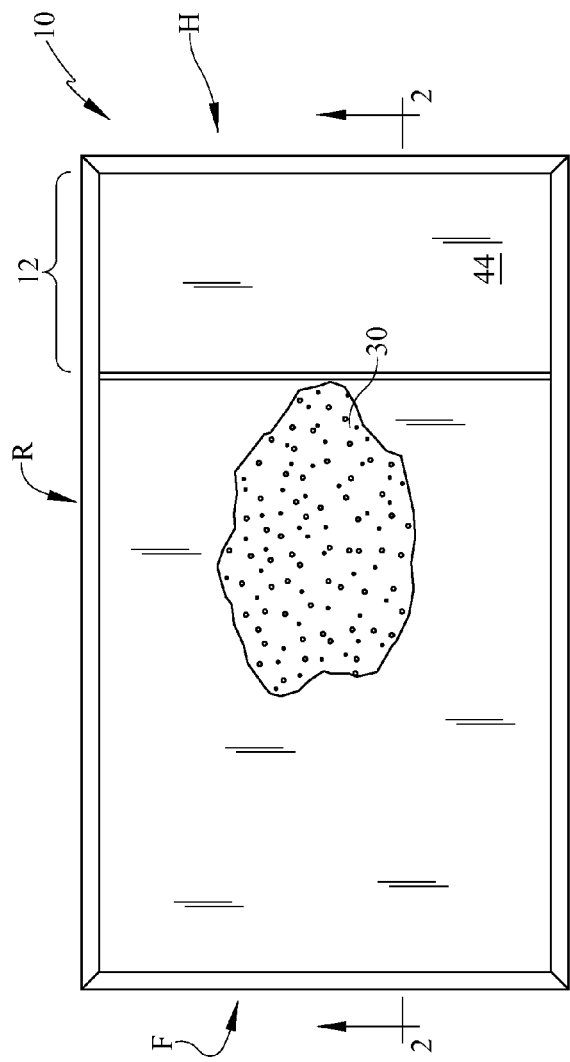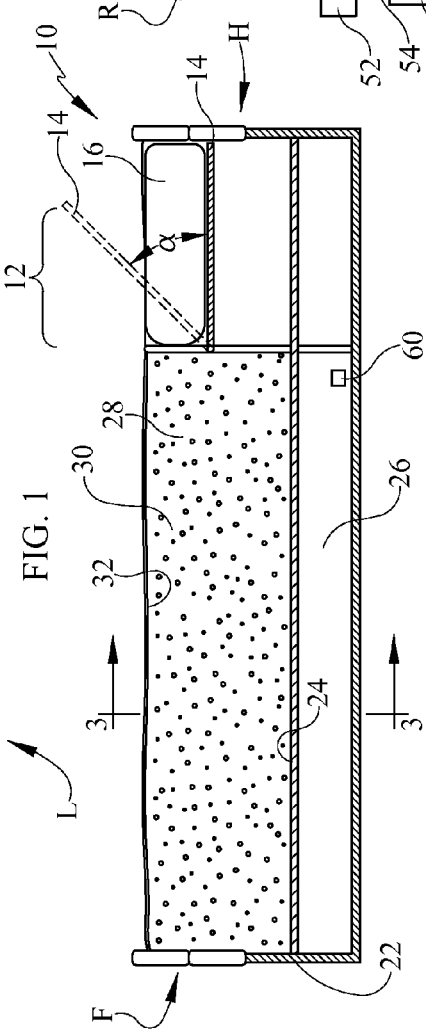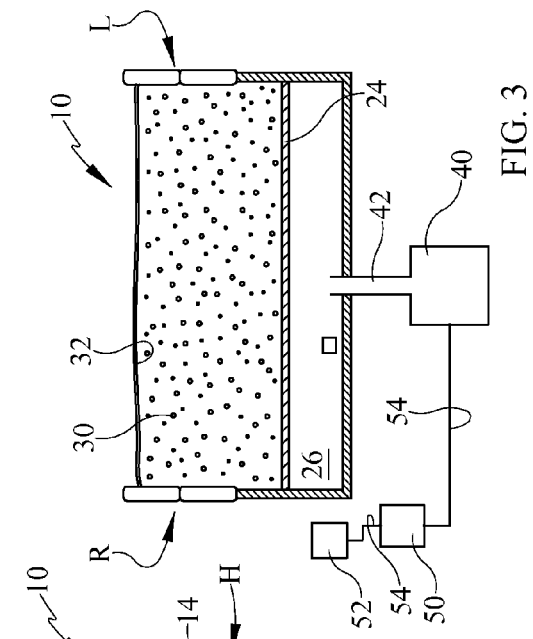

FLUIDIZABLE BED WITH OCCUPANCY STATUS DETECTION AND METHOD OF OCCUPANCY STATUS DETECTION FOR A FLUIDIZABLE BED

TECHNICAL FIELD

The subject matter described herein relates to fluidizable beds and particularly to a fluidizable bed having the capability to detect occupancy status and changes thereof and to an associated method of occupany status detection. In an example application the capability and method are employed to detect if a person expected to be occupying the bed has exited the bed.

BACKGROUND

A typical fluidizable bed includes a receptacle and a porous diffuser board that divides the receptacle into a plenum and a fluidizable medium container above the plenum. A fluidizable medium, such as tiny spherical particles, occupies the fluidizable medium container. A filter sheet overlies the fluidizable medium. In operation a fluidizing medium such as ambient air is pressurized and introduced into the plenum. The air flows through the diffuser board, through the fluidizable medium, and exhausts through the filter sheet. The flow of air through the fluidizable medium imparts fluid-like properties to the fluidizable medium so that the medium acts as a quasi-fluid. Fluidizable beds are used for burn victims or other patients who have skin disorders such as pressure ulcers or who are at high risk of developing skin disorders as a result of long term confinement in bed. Some fluidizable beds include a more conventional, non-fluidizable upper body or torso section corresponding approximately to the torso of a bed occupant.

Despite the advantages of fluidizable beds they do not offer certain capabilities which are not uncommon in more conventional beds. One such capability is an occupancy status detection capability which can detect the presence or absence of an occupant and changes in that status. Occupancy status capability is typically used to alert a caregiver of the unauthorized departure of the bed occupant from the bed.

SUMMARY

A fluidizable bed comprises a receptacle, a diffuser board dividing the receptacle into a fluidizable medium container and a distribution plenum beneath the fluidizable medium container, the fluidizable medium container adapted to receive a quantity of a fluidizable medium and the plenum adapted to receive a stream of a fluidizing medium such that the fluidizable medium is fluidized as a result of admission of the fluidizing medium to the plenum. The bed also includes a pressure sensor for monitoring a pressure value representative of pressure in the plenum and a controller for issuing a signal responsive to a relationship between the monitored value and a reference value.

A related method of detecting a change in occupancy status of a fluidizable bed includes determining an unloaded plenum pressure value corresponding to the absence of a load on the bed, determining a loaded plenum pressure value corresponding to the presence of an occupant on the bed, and establishing a reference as a function of at least one of the unloaded plenum pressure value and the loaded plenum pressure value. A signal is issued in response to a relationship between the reference and a value representative of actual pressure in the plenum.

BRIEF DESCRIPTION OF THE DRAWINGS

The foregoing and other features of the various embodiments of the fluidizable bed described herein will become more apparent from the following detailed description and the accompanying drawings in which:

FIG. 1 is a schematic plan view of a fluidizable bed with a filter sheet component of the bed partly broken away to reveal a fluidizable medium beneath the filter sheet.

FIG. 2 is a side elevation view taken in the direction 2-2 of FIG. 1.

FIG. 3 is a foot end elevation view taken in the direction 3-3 of FIG. 2.

DETAILED DESCRIPTION

Figure 4:
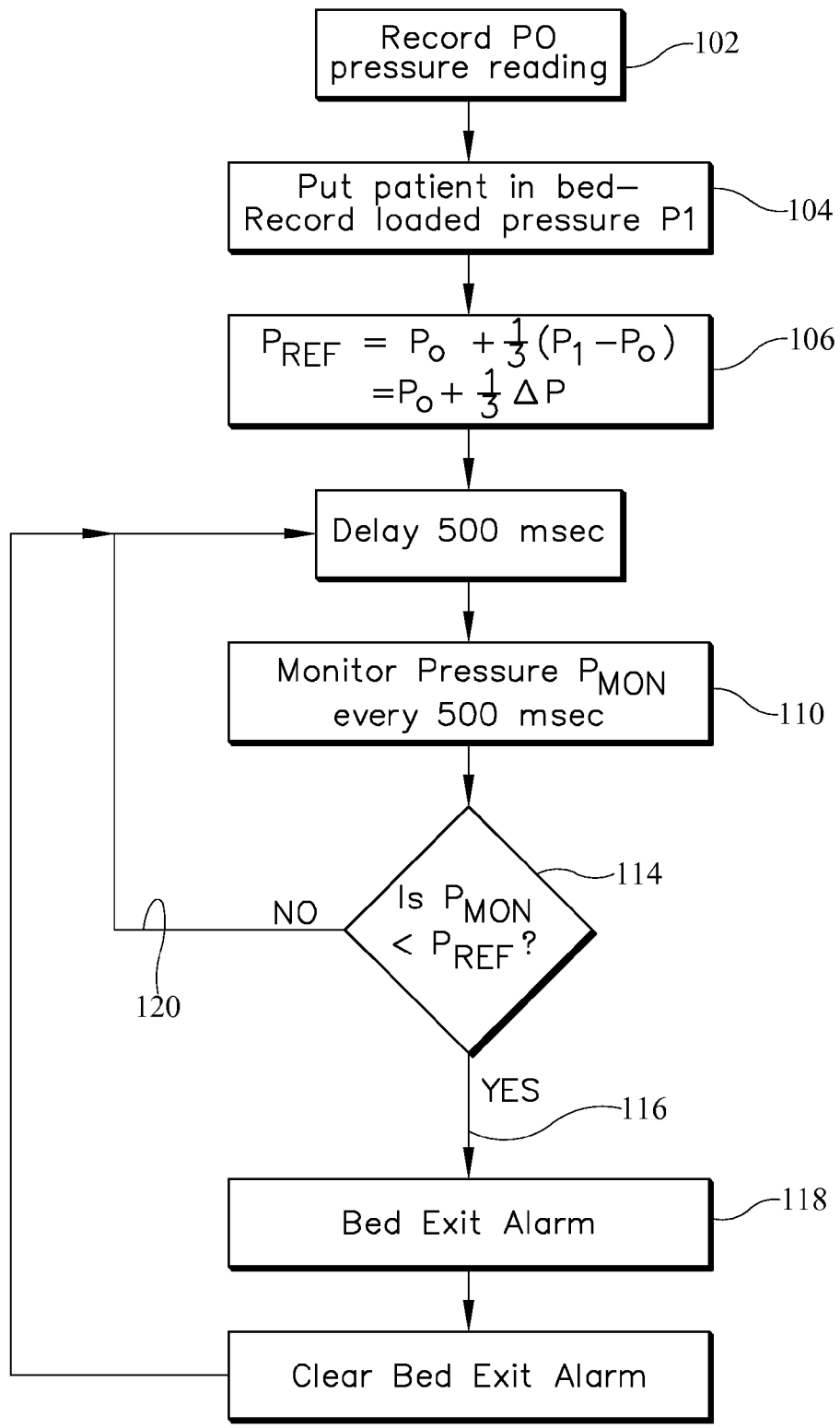
FIGS. 4-5 are block diagrams of variants of an occupancy status detection method disclosed herein in which the method is based on a pressure difference between the occupied state and the unoccupied state.

Referring to FIGS. 1-3 a fluidizable bed 10 extends longitudinally from a head end H to a foot end F and laterally from a left side L to a right side R. An upper body or torso section 12 of the bed corresponds approximately to the torso of a bed occupant. The upper body section is a nonfluidizable section and includes a deck section 14 and a mattress 16 resting on the deck section. The deck can be pivoted to an orientation angle α between about 0° (horizontal) shown with solid lines) and about 65°-70° shown with dashed lines. A fluidizable section of the bed comprises a receptacle 22 and a porous, gas permeable diffuser board 24 dividing the receptacle into a distribution plenum 26 and a fluidizable medium container 28. A fluidizable medium 30 resides in the container. A porous filter sheet 32 overlies the fluidizable medium. A blower 40 is connected to plenum 26 by a conduit 42. A controller 50 controls operation of the blower to control admission of a fluidizing medium, typically ambient air pressurized by the blower, to plenum 26. A user interface 52 receives instructions for the controller from a user such as an occupant or caregiver. The illustration suggests the use of physical communication paths 54 between the blower, controller and user interface, however wireless communication could be used instead.

When the blower operates, the fluidizing medium is admitted to plenum 26, flows upwardly through pores in diffuser board 24, through the fluidizable medium 30, and is then exhausted to the environment through pores in filter sheet 32. The flow of fluidizing medium through the fluidizable medium imparts fluid-like properties to the fluidizable medium. An occupant of the bed is therefore supported by his or her buoyancy in the fluidized medium.

A pressure sensor 60 is installed in plenum 26. Alternatively the sensor could be installed in some other location such as in conduit 42 so that it senses or monitors a pressure representative of the pressure of the fluidizing medium in the plenum. Examples of representative pressures include pressure in the plenum itself and pressure in conduit 42. Pressures sensed at other locations upstream of diffuser board 24 are also representative pressures.

Figure 6:
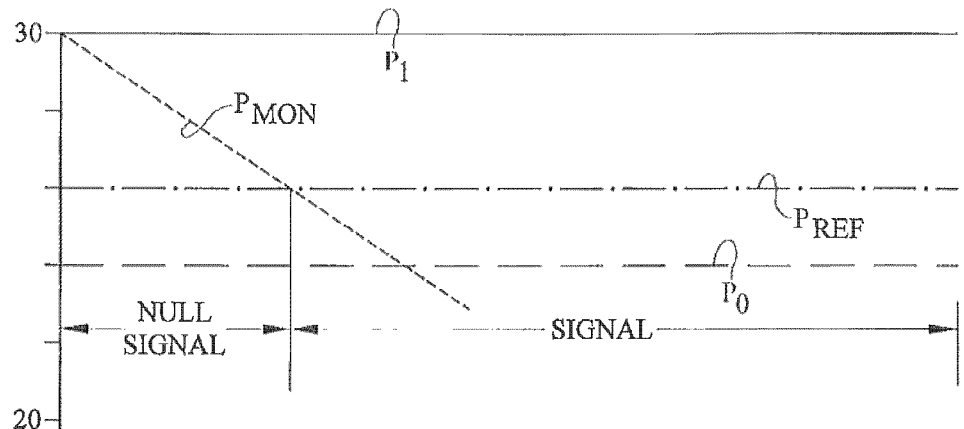
FIGS. 6-7 are graphs illustrating operation of the occupancy status detection method of FIGS. 4-5.

FIG. 4 is a block diagram illustrating a method of detecting occupancy status of a fluidizable bed. FIG. 6 is a simple graphical illustration of the method of FIG. 4 with pressure expressed in inches of water shown on the vertical axis and time on the horizontal axis. The numerical pressure values along the vertical axis are approximate and illustrative only. At block 102 the method determines an unloaded plenum pressure value $P_0$, for example by using the pressure reading from sensor 60. The unloaded plenum pressure value corresponds to the absence of a load, such as an occupant, on the bed with the fluidizable medium in its fluidized state.

At block 104 the method determines a loaded plenum pressure value, for example by using the pressure reading from sensor 60. The loaded plenum pressure value is determined after an occupant is resting on the bed with the fluidizable medium in its fluidized state and is greater than the unloaded value. The loaded plenum pressure value may be determined with torso section 12 (FIG. 1) at any orientation, however applicants believe that best results will be obtained if the torso section, and therefore the torso of the occupant is at an orientation angle α of about 0°.

At block 106 the method establishes a reference $P_{REF}$ as a function of at least one of the unloaded plenum pressure value and the loaded plenum pressure value. The illustrated reference equals the unloaded plenum pressure value $P_0$ plus a fraction f of the difference between the loaded plenum pressure value $P_1$ and the unloaded plenum pressure value $P_0$. In the method as illustrated in the block diagram the fraction is one third. Expressed algebraically:

$$P_{REF}=P_0+\tfrac{1}{3}(P_1-P_0)=P_0+\Delta P/3 \quad [1]$$

At block 110 the method begins monitoring the representative pressure. The illustrated monitoring frequency is once every 500 milliseconds. At block 114 the method issues a signal in response to a relationship between the reference $P_{REF}$ and the value $P_{MON}$ representative of actual pressure in the plenum. Specifically the method compares the monitored representative pressure $P_{MON}$ to the reference $P_{REF}$. If $P_{MON}$ is less than $P_{REF}$ the issued signal 116 is conveyed to one or more destinations 118. Examples of such destinations include an aural alarm unit, a visual alarm unit, a nurse station, and an electronic medical record. If $P_{MON}$ is not less than $P_{REF}$, the method does not issue signal 116, which can be considered to be the issuance of a NULL signal 120, in which case the method continues to carry out the steps at blocks 110, 114. It will be appreciated that the "less than" operator at block 114 can be replaced with a "less than or equal to" operator.

Figure 5:
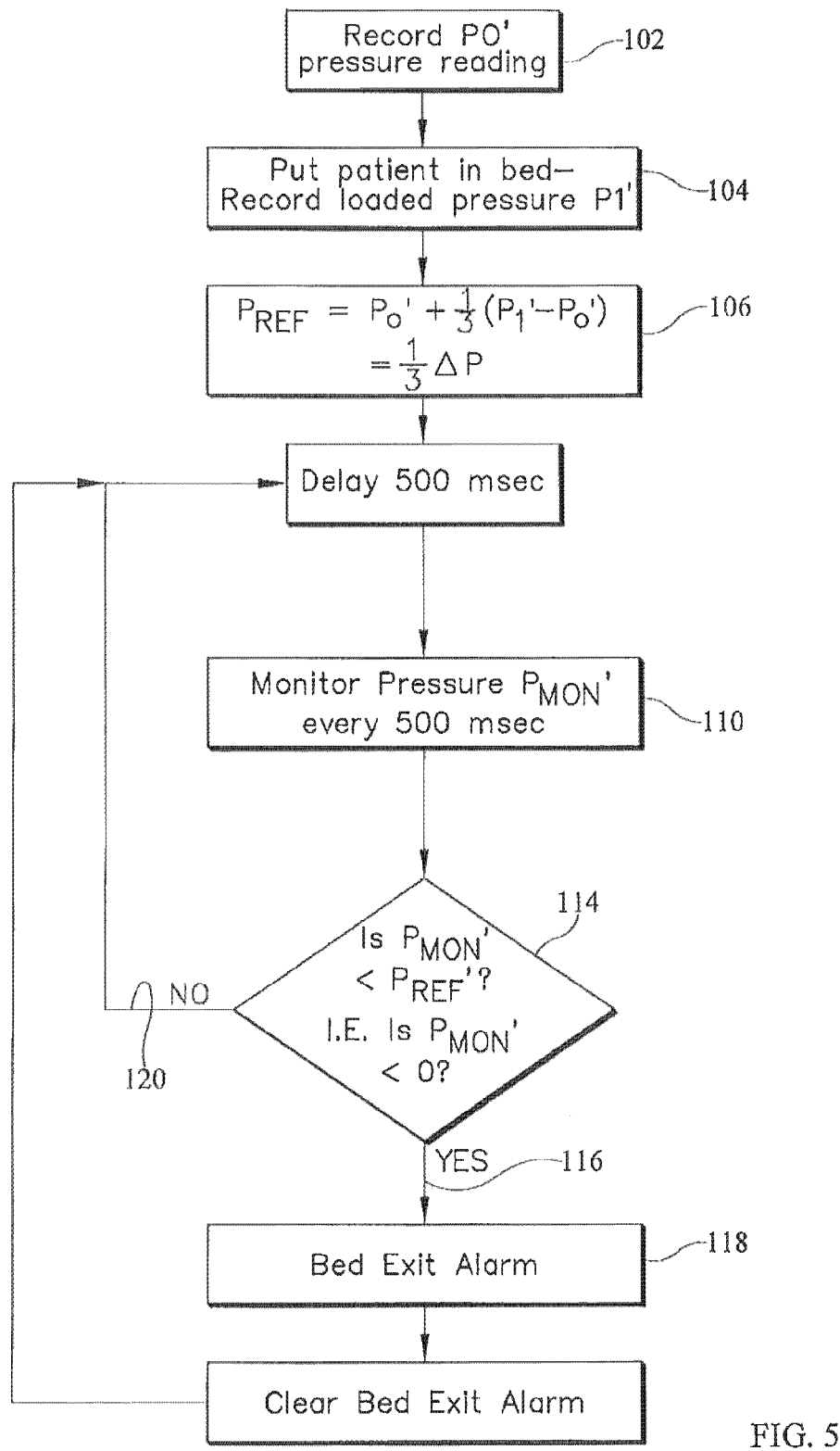
Figure 7:
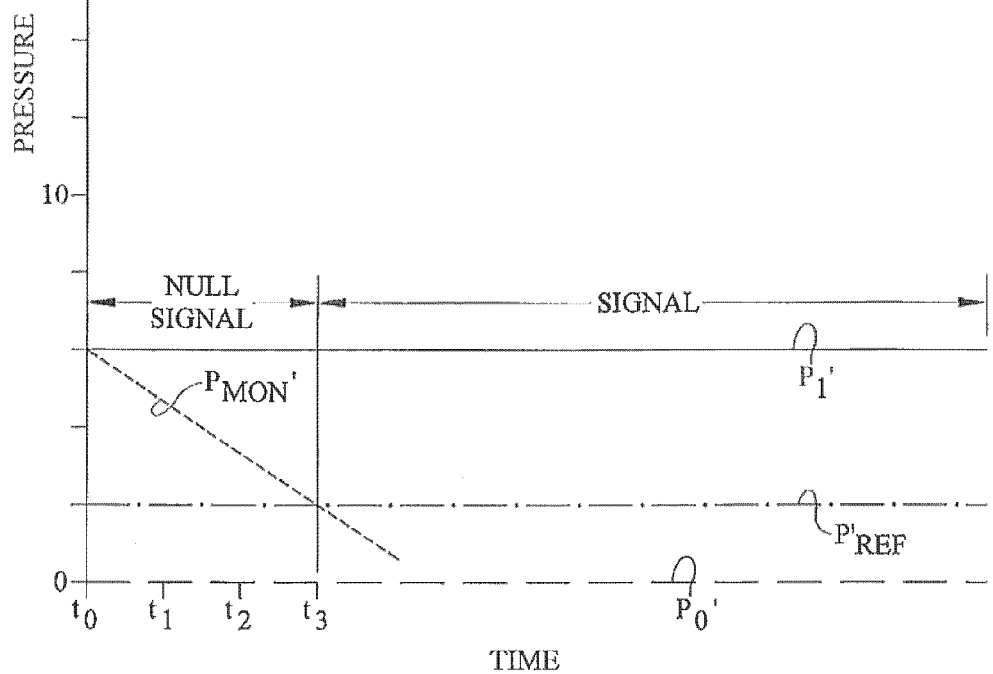

FIGS. 5 and 7 are a block diagram and graph, similar to FIGS. 4 and 6, illustrating a variant of the method. At block 102 the method determines an unloaded plenum pressure value P0' which is a "zeroed" equivalent of the actual monitored pressure $P_0$ from sensor 60. In other words $P_0$' is an offset value:

$$P_0'=P_0-P_0=0 \quad [2]$$

Other pressure readings will be similarly offset by $P_0$ as signified by the use of the prime superscript in FIGS. 5 and 7. The unloaded plenum pressure value $P_0$' corresponds to the absence of a load, such as an occupant, on the bed with the fluidizable medium in its fluidized state. 7.

At block 104 the method determines a loaded plenum pressure value $P_1$', for example by using the pressure reading from sensor 60 offset by $P_0$. As with the previously described variant, the loaded plenum pressure value is determined after an occupant is resting on the bed with the fluidizable medium in its fluidized state. The loaded plenum pressure value may be determined with torso section 12 at any orientation, however applicants believe that best results will be obtained if the torso section, and therefore the torso of the occupant is at an orientation angle α of about 60°.

At block 106 the method establishes a reference $P_{REF}$' as a function of at least one of the unloaded plenum pressure value and the loaded plenum pressure value. The illustrated reference equals the unloaded plenum pressure value $P_0$' plus a fraction (e.g. one third) of the difference between the loaded plenum pressure value $P_1$' and the unloaded plenum pressure value $P_0$'.

$$P_{REF}'=P_0'+\tfrac{1}{3}(P_1'-P_0')=\Delta P/3 \quad [3]$$

At block 110 the method begins monitoring the representative pressure once every 500 milliseconds. Because of the "zeroing" of the pressure readings at blocks 102 and 104, the monitored pressure reading reflects the same offset and therefore is designated $P_{MON}$'. Similarly, the term on the right side of the inequality at block 114 is $P_{REF}$':

$$P_{REF}'=P_{REF}-\Delta P/3=0 \quad [4]$$

At block 114 the method issues a signal in response to a relationship between the reference $P_{REF}$' and the value $P_{MON}$' representative of actual pressure in the plenum. Specifically the method compares the monitored representative pressure $P_{MON}$' to the reference $P_{REF}$'. If $P_{MON}$' is less than $P_{REF}$' the issued signal 116 is conveyed to one or more destinations as already described. If $P_{MON}$' is not less than $P_{REF}$', the method does not issue signal 116, which, as previously noted, can be considered to be the issuance of a NULL signal 120, in which case the method continues to carry out the steps at blocks 110, 112, 114. It will be appreciated that the "less than" operator at block 114 can be replaced with a "less than or equal to" operator.

Figure 8:
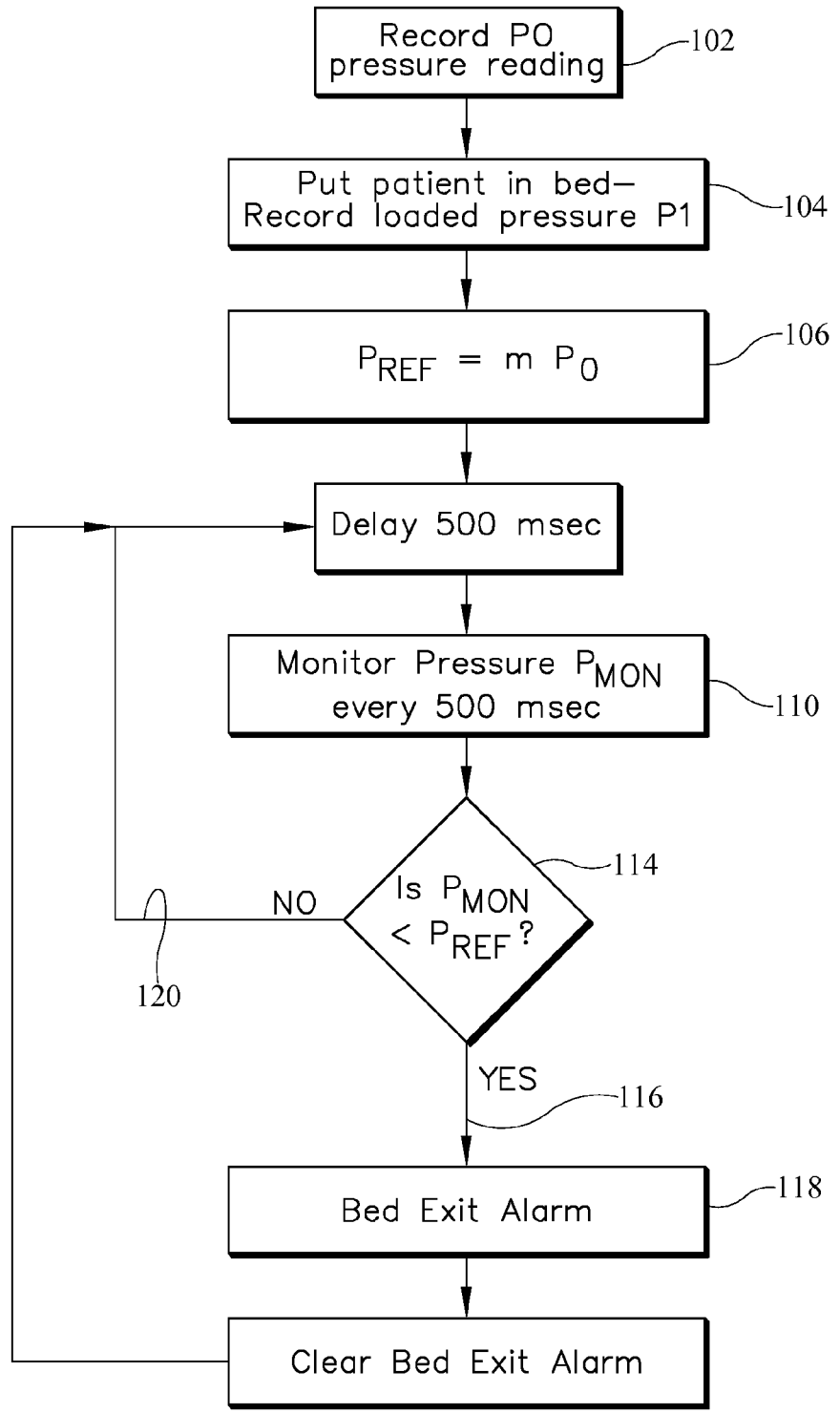
FIG. 8 is a block diagram of another variant of the occupancy status detection method disclosed herein in which the method is based on a fraction of a loaded pressure or a fraction of an unloaded pressure.

FIG. 8 shows another variant in which the step of establishing a reference (block 106) involves determining a multiple m (which may be a nonintegral multiple) of the unloaded plenum pressure value $P_0$ (as shown) or a fraction $f_1$ of the loaded plenum pressure value $P_1$, for example:

$$P_{REF}=mP_0 \text{ where } 1.0<m<P_1/P_0, \text{ or}$$

$$P_{REF}=f_1P_1 \text{ where } f_1<1.0$$

where m and $f_1$ are the chosen multiple and fraction.
As in the other examples the issuing step at block 114 comprises issuing signal 116 in response to the representative value being less than the reference or less than or equal to the reference or otherwise issuing a NULL signal 120.

Although this disclosure refers to specific embodiments, it will be understood by those skilled in the art that various changes in form and detail may be made without departing from the subject matter set forth in the accompanying claims.

We claim:
1. A method of detecting a change in occupancy status of a fluidizable bed extending longitudinally between a head end and a foot end and having a distribution plenum and a fluidizable medium, the method comprising:
  determining an unloaded plenum pressure value corresponding to an absence of a load on the bed;
  determining a loaded plenum pressure value corresponding to a presence of an occupant on the bed, wherein the unloaded plenum pressure and the loaded plenum pressure are determined using a pressure sensor that is installed either inside the plenum or a conduit that connects a blower with the plenum such that the entirety of the sensor is situated inside the plenum or conduit, wherein the plenum is continuously open to atmosphere through the fluidizable medium when the unloaded plenum pressure and the loaded plenum pressure are measured by the pressure sensor;

calculating a reference value as a sum of the unloaded plenum pressure value and a predetermined fraction of a difference between the loaded and unloaded plenum pressure values, wherein the unloaded plenum pressure value corresponds to pressure in the plenum when the fluidizable medium is in a fluidized state and a load is not being supported by the fluidized medium, and the loaded plenum pressure value corresponds to fluid pressure in the plenum when the fluidizable medium is in the fluidized state and a portion of the occupant is supported by the fluidized medium with another portion of the occupant being supported by a nonfluidizable section of the bed that is pivotable upwardly and downwardly relative to a fluidizable medium container that contains the fluidizable medium, the nonfluidizable section being situated adjacent the head end of the fluidizable bed and the fluidizable medium container being configured so that the fluidizable medium occupies a space extending from the nonfluidizable section to the foot end of the fluidizable bed;

detecting a current pressure value in the plenum; and issuing a signal in response to the current pressure value being equal to or less than the reference value.

2. The method of claim 1 wherein the predetermined fraction is one third.

3. The method of claim 1 wherein the unloaded plenum pressure value and the loaded plenum pressure value are offset.

4. A fluidizable bed extending longitudinally between a head end and a foot end, the fluidizable bed comprising:
   a blower;
   a receptacle;
   a diffuser board dividing the receptacle into a fluidizable medium container and a distribution plenum beneath the fluidizable medium container, the fluidizable medium container adapted to receive a quantity of a fluidizable medium and the plenum adapted to receive a stream of a fluidizing medium from the blower via a conduit that extends between the blower and the plenum such that the fluidizable medium is fluidized as a result of admission of the fluidizing medium to the plenum;
   a pressure sensor for monitoring a value representative of pressure in the plenum;
   and a controller configured to calculate a reference pressure value as a sum of an unloaded plenum pressure value and a fraction of a difference between a loaded plenum pressure value and the unloaded plenum pressure value, and for issuing a signal indicating that a current plenum pressure is less than or equal to the reference pressure value, wherein the unloaded plenum pressure value corresponds to pressure in the plenum when the fluidizable medium is in a fluidized state and a load is not being supported by the fluidized medium, and the loaded plenum pressure value corresponds to pressure in the plenum when the fluidizable medium is in the fluidized state and a portion of an occupant is supported by the fluidized medium with another portion of the occupant being supported by a nonfluidizable section of the bed that is pivotable upwardly and downwardly relative to the fluidizable medium container, the nonfluidizable section being situated adjacent the head end of the fluidizable bed and the fluidizable medium container being configured so that the fluidizable medium occupies a space extending from the nonfluidizable section to the foot end of the fluidizable bed, wherein the pressure sensor is installed either inside the plenum or the conduit such that the entirety of the sensor is situated inside the plenum or conduit, wherein the plenum is continuously open to atmosphere through the fluidizable medium when the unloaded plenum pressure and the loaded plenum pressure are measured by the pressure sensor.

5. The fluidizable bed of claim 4 wherein the fraction is one third.

6. The fluidizable bed of claim 4 wherein the unloaded plenum pressure value and the loaded plenum pressure value are offset values.

7. A fluidizable bed extending longitudinally between a head end and a foot end, the fluidizable bed comprising:
   a blower;
   a receptacle;
   a diffuser board dividing the receptacle into a fluidizable medium container and a distribution plenum beneath the fluidizable medium container, the fluidizable medium container adapted to receive a quantity of a fluidizable medium, and the plenum arranged continuously open to atmosphere through the fluidizable medium and adapted to receive a stream of a fluid from the blower connected with the plenum such that the fluidizable medium is fluidized as a result of admission of fluid to the plenum;
   a pressure sensor arranged for monitoring pressure in the plenum; and
   a controller configured to calculate a threshold pressure value as a sum of an unloaded plenum pressure value and a predetermined fraction of a difference between a loaded plenum pressure value and the unloaded plenum pressure value,
   wherein the unloaded plenum pressure value corresponds to pressure in the plenum having the fluidizable medium in the fluidized state and an occupant load is not supported by the fluidized medium, and the loaded plenum pressure value corresponds to pressure in the plenum having the fluidizable medium in the fluidized state and at least a portion of an occupant is supported by the fluidizable medium.

8. The fluidizable bed of claim 7, wherein the predetermined fraction is one third.

9. The fluidizable bed of claim 7, wherein the predetermined fraction is calculated by the controller as a function of the unloaded and loaded plenum pressure values.

10. The fluidizable bed of claim 7, wherein the unloaded plenum pressure value and the loaded plenum pressure value are offset.

11. The fluidizable bed of claim 7, wherein the controller is configured to issue a signal indicating an alarm to activate when a current pressure value is less than the threshold pressure value.

* * * * *